US009808396B2

(12) United States Patent
Ferrari et al.

(10) Patent No.: US 9,808,396 B2
(45) Date of Patent: Nov. 7, 2017

(54) ELECTROMECHANICAL MACHINE WITH WIRELESS CONTROL FOR SEXUAL ACTIVITY

(71) Applicant: RECICLAYRES S.A., Ciudad de Buenos Aires (AR)

(72) Inventors: Carlos Isidoro Ferrari, Ciudad de Buenos Aires (AR); Reynaldo del Rio, Ciudad de Buenos Aires (AR)

(73) Assignee: Reciclayres S.A., Ciudad de Buenos Aires (AR)

( * ) Notice: Subject to any disclaimer, the term of this patent is extended or adjusted under 35 U.S.C. 154(b) by 233 days.

(21) Appl. No.: 14/862,442

(22) Filed: Sep. 23, 2015

(65) Prior Publication Data

US 2016/0367431 A1 Dec. 22, 2016

(30) Foreign Application Priority Data

Jun. 17, 2015 (AR) .............................. 20150101925

(51) Int. Cl.
*A61F 5/00* (2006.01)
*A61H 19/00* (2006.01)

(52) U.S. Cl.
CPC ...... *A61H 19/44* (2013.01); *A61H 2201/0119* (2013.01); *A61H 2201/0161* (2013.01);
(Continued)

(58) Field of Classification Search
CPC ........ A61H 19/00; A61H 19/40; A61H 19/44; A61H 19/50
(Continued)

(56) References Cited

U.S. PATENT DOCUMENTS 5,076,261 A * 12/1991 Black .................... A61H 19/44 601/93
6,179,795 B1 * 1/2001 Garza .................... A61H 19/44 600/38

(Continued)

*Primary Examiner* — John Lacyk
(74) *Attorney, Agent, or Firm* — The Morales Law Firm, LLC; Joseph L. Morales

(57) ABSTRACT

A machine that combines three sections bound to each other by the corresponding dynamic swivels that are driven from a remote control of adjustment and command (R). The first section constitutes the main body (A) wherein a fixed frame whereby a sliding carriage (D) is defined, which is arranged associated with a first motor reducer (M1) which drives its rectilinear movement, in the horizontal plane and in both senses; said sliding carriage (D), by one end, is bound to an intermediate arm (B), which makes up the second section of the machine, being arranged over a pivoting transverse axis that is into a first dynamic swivel, which is arranged associated to a second driving motor reducer (M2) so that said intermediate arm (B) may make a pivoting movement in the vertical plane, with circular direction in both senses; said intermediate arm (B), by its other end, is bound to a head of the massage actuator (C), that makes up the third section of the machine, being arranged over a transverse axis that forms a second dynamic swivel, which is arranged associated to a third driving motor reducer (M3) so that said head of massage actuator may make a pivoting movement in the vertical plane, with circular direction in both senses; an actuator piston (P) is arranged into the head of the massage actuator (C) which transforms the rotating movement that transmits the output axis of a fourth motor reducer into an alternative linear movement that is transmitted to the piston for massage (23); constituting the four motor reducers an electronic driving installation by remote control, through which the positioning of each of the mobile parts duly bound to the rotating coders and end-of-travel positions is commanded. The electronic driving installation is comprised of (Continued)

the electronic controlling plate (E) installed in the main body (A) and includes a remote control processor (MP2) that receives the order, processes the information and sends it through the FR antenna (a4) of the remote control (R), to the FR antenna (a1) of the electronic system (E) installed into the machine, that communicates the information to its processor (MP1). The electronic installation of remote control includes the option of saving, through memories, the previous adjustment that the user establishes in each case.

8 Claims, 9 Drawing Sheets

(52) U.S. Cl.
CPC ................ *A61H 2201/1207* (2013.01); *A61H 2201/1238* (2013.01); *A61H 2201/1463* (2013.01); *A61H 2201/1664* (2013.01); *A61H 2201/1676* (2013.01); *A61H 2201/50* (2013.01); *A61H 2201/501* (2013.01); *A61H 2201/5012* (2013.01); *A61H 2201/5051* (2013.01); *A61H 2201/5056* (2013.01); *A61H 2201/5069* (2013.01); *A61H 2201/5084* (2013.01); *A61H 2205/087* (2013.01)

(58) Field of Classification Search
USPC ...................................................... 600/38–41
See application file for complete search history.

(56) References Cited

U.S. PATENT DOCUMENTS

| | | | | |
|---|---|---|---|---|
| 6,632,185 | B2 | 10/2003 | Chen | |
| 6,866,645 | B2 * | 3/2005 | Lee | A61H 19/44<br>600/38 |
| 6,890,293 | B2 * | 5/2005 | Kobayashi | A61H 19/44<br>128/845 |
| 6,902,525 | B1 | 6/2005 | Jewell | |
| 7,175,592 | B2 | 2/2007 | Lee | |
| 7,267,646 | B2 * | 9/2007 | Tucker | A61H 19/44<br>600/38 |
| 2005/0228219 | A1 | 10/2005 | Jewell | |

* cited by examiner

ELECTROMECHANICAL MACHINE WITH WIRELESS CONTROL FOR SEXUAL ACTIVITY

CROSS REFERENCE TO RELATED APPLICATIONS

This application claims the priority benefit under 35 U.S.C. §119(a) of Argentinean patent application serial number 20150101925 filed on Jun. 17, 2015, and entitled "Electromechanical Machine with Wireless Control for Sexual Activity"; which is incorporated herein by reference in its entirety.

BACKGROUND OF THE INVENTION

Field of the Invention

The present invention relates to the field of mechanical devices and, more specifically to electromechanical devices for sexual stimulation.

Background

It may be stated that mechanical sexual toys usually named "sex machines" and "fucking machines" are found on a large scale in the market of products for adults; there exists any type of models and variants related to the operation, use, aesthetic and comfort of these machines, turning a really complicated task to select and decide which is the best one to be used.

Most of these models are mainly intended to self satisfaction and are preferably used by women.

Tables with heights, widths, extensions, possibility of easy assembly and removal, systems of articulated profiles, manual fixing with screws and use of tools, controls with sliding rails, small power supplies and else elements intending to attract and convince the buyer that the task of setting up the machine at the time of being used is comfortable, pleasant and fast.

However, in view of the great amount of opinions, claims and also complaints against what is disclosed in the Internet pages promoting these machines, as well as what is learned from the amateurs' forums, today it is known the difficult task of the user, both men and women, to start using these machines in general.

It is known the excessive time required to establish the preferred position to use it, where it is worthwhile mentioning the difficult task of adjusting the swivels, either by manually fixing the pins or screws and tools, as well as the time being necessary for the assembly and removal of the device.

It is also worthwhile mentioning, that in most cases, undesirable deviations of the set-up occur at the very beginning of use as a result of the vibrations. It is also worthwhile mentioning the little friendly aesthetic aspect, with designs and forms that look more like a torture machine than one intended to give pleasure. In this sense, various invention patents are known that describe and protect specific realizations, among which the following may be mentioned:

US 20050228219 A1 discloses an enlarged portable device and of a cylindrical shaping, very light and able to produce a rotating movement and to transform said movement into an alternative linear movement, which is transmitted to a cylindrical device of self stimulation or masturbation. This is a device comprising of an assembly of power transmission including an axle-drive with connection means associated therewith in order to bind itself to an energy source, wherein the same axle is linked to an external rotating body which is fit to be inserted to transmit the movement to a device of self stimulation of a linear driving comprising of a cylindrical shuttle connected to and coaxial with said transmission and adapted to receive rotating energy and transform said energy into a rectilinear movement of linear driving.

Said energy transmission assembly includes a corresponding gearbox containing at least two gears that are combined with the assembly of linear driving, which in turn includes a clutch and a set of cam and groove.

U.S. Pat. No. 6,902,525 B1 teaches an electromechanical device which is fed from an external energy source, capable to generate a rotating movement and in turn a forward and backward movement, usually defined as a wireless electric screw driver and capable to transmit that rotating and alternative linear movement to sexual devices used for men and women with the purpose of masturbation and self stimulation. This is a substantial cylindrical device that combines a rotating movement for stimulation with a linear alternative movement also for stimulation, supporting that it is a very satisfactory movement.

The invention emphasizes that it is a simple, light, small, potent, low cost device that can be used with only one hand; it is hygienic, of a neutral orientation, neutral sexual gender, comfortable, strong, secure, reliable, totally waterproof, and of a sexually pleasant versatile positioning.

U.S. Pat. No. 6,632,185 B2 discloses a device for massages, and more particularly an extensible and rotating device for massages. The device for massage has a rotating axis with curved grooves defined over the rotating axis periphery, and a guide being driven by curved grooves in such a way that when the rotating tree rotates, the guide is capable of causing a linear movement together with the rotating axis movement.

U.S. Pat. No. 7,175,592B2 discloses a mechanical device for massages comprising of a pedestal over which a main body is arranged having a special structure assembled in a sliding condition on the main body, having a first end projecting from said main body that may be arranged forward or backward thereof, which holds a removable piece of massage. The device includes a sliding rack located into the main body, a chain with a mobile lock projected and inserted into a groove defined in the rack and an engine to control and operate the chain in such a way that the movement of the mobile lock projecting therefrom causes the linear swinging movement.

SUMMARY OF THE INVENTION

The present invention, which invention patent is being applied for, refers to an ELECTROMECHANICAL MACHINE WITH WIRELESS CONTROL FOR SEXUAL ACTIVITY specially distinguished because it combines three sections bound to each other via dynamic electromechanical swivels of remote control, allowing the user to determine various positions and functions in a simple and direct way.

More specifically, the present invention refers to a machine for sexual activity having as its main characteristic the possibility for the user to start-up the device in a simple and direct way by using a remote control; thus being avoided the initial tiresome task of positioning and fitting the machine before the use thereof.

It consists of a machine that, being of a simple use, is fit in such a way that it may be used by a wide range of different people generations and also different bodies, including those users that are not familiarized with this kind of products, with no visible connection cables, as, preferably, this machine works with rechargeable batteries that may be connected to the mains power supply after being used.

The invention machine is also different because the above mentioned dynamic electromechanical swivels, by being linked to a remote control, provide the possibility of establishing a personalized positioning and working by way of memories that are set by the user himself/herself while different ways of use are discovered.

In effect, the invention refers to a novel sexual machine having the capacity to adjust to a great variety of angles and positions chosen by the user in a simple and direct way by only using the remote control and not being necessary to put into contact with the machine; an additional advantage is that, once chosen a preferred position, such position may be introduced in the memory so that at the time of using it again, it may be directly established by using the remote control.

The three sections bound to each other that constitute the machine of this invention, are comprised of:

- a lower support base containing the main body which can be horizontally moved in a straight direction and in a forward and backward sense;
- this main body, through a first dynamic swivel, is bound to an intermediate arm; said arm is projected from the extreme thereof and may be moved in an angular way over a vertical plane and therefore getting inclined positions as regards the horizontal plane;
- the third section is a head into the massage actuator, that is bound to the referred intermediate arm through a second dynamic electromechanical swivel, in this case said swivel was adapted to take different angular positions in the vertical plane, while the piston for massage which has been designed to make the traditional rectilinear swinging movement, keeps its capacity to regulate the speed and run. This piston is assembled in a replaceable condition in order to allow the incorporation of various models of various formats and sizes, through the direct coupling means supplied with the machine.

This is a clearly distinguished machine because, in addition to being comfortable and simple to be kept and carried, it introduces a novel electromechanical device with a specific electronic drive and control, highly efficient and pleasant for users, above all because it introduces the possibility of the remote control, which is an additional benefit to the special comforting design thereof which brings a pleasant aspect to the device so as not to cause fear, reject or hurt feelings to the users (as if it were a torture instrument).

This is an invention that defines a new combination of means devised to get a top result, being an unpredictable and surprising invention even for those skilled in the art. Accordingly, in addition to the novelty, its constructive and functional structure shows a clear inventive activity so as to be considered an invention patent as it meets all the requirements established by the Patents Act.

Nothing in the above background discloses, teaches or suggests how to devise an electromechanical machine for sexual activity combining three sections bound to each other through dynamic swivels that are driven with a remote control so that the user may regulate in an efficient, quick, simple and personalized way the preferred position and removing all the difficulties previously described; as well as how to grant a considerable increase in the piston run that produces the rectilinear movement intended to pretend the sexual act, including regulating the swinging movement speed, which is also controlled with a remote control.

In effect, the electromechanical machine for sexual activity which is referred to by the present invention comprises of a first section wherein the main body is defined as constituted over a base that, preferably, is supplemented with a flat platform, to provide a stable support to the assembly.

A special sliding carriage is arranged over said main body in the horizontal plane that, to such effect, is kept bound to an electric motor reducer through a thread nut sliding over a thread axis that constitutes a worm duly coupled to the outlet of said motor reducer.

Specifically, the rectilinear movement is possible through the mentioned motor reducer, in both senses of the mentioned carriage, in the horizontal plane, for which also the corresponding electronic sensors are included; said electronic sensors allow the establishment of the positioning run that may be adopted by the carriage on the lower support flat base.

In preferred embodiments, the electronic installation of general control is also arranged on the same base of the main body for the driving assembly and its wireless binding to the external devices of remote control, including the possibility of introducing already known means to interact with internal and external communication networks.

Said sliding carriage, by one end, is bound to the above mentioned intermediate arm through a first dynamic swivel that provides the second adjustment of the previous positioning.

This first swivel allows the intermediate arm to make a pivoting movement in the vertical plane, with circular direction and also in both senses. The movement is driven by the second motor reducer which output axis is associated with a gear train and a corresponding assembly of crown and worm; said motor also makes up the mentioned electronic installation of remote control drive.

Additionally, the referred intermediate arm, by the other end, is associated with a second dynamic swivel that binds said arm to the third section, which constitutes the head of the massage actuator.

With this second dynamic swivel, it is also caused the referred head of the massage actuator to carry out the pivoting movement in the vertical plane, with a circular direction and in both senses, so that the user may establish a previous preferred position thereof.

In this case, the movement is driven by the second motor reducer which output axis is associated with a gear train and a corresponding assembly of crown and worm wherein said motor also makes up the mentioned electronic driving installation of remote control drive. Furthermore, the mechanical assembly named piston is located into the head of the massage actuator, which function is to transform the rotating movement that is transmitted by the output axis of a motor into a linear alternative movement that is transmitted to the massage piston.

So, the output axis of a fourth motor reducer is associated with a hollow axis which cylindrical surface is affected by a longitudinal groove that follows a curved line such as a continuous sinusoidal propeller (worm).

Above said helical groove, a sliding skid runs, conveniently assembled over bearings, which is associated with the cylindrical and enlarged body of the massage piston, and provides the traditional swinging linear movement. The run of this massage piston, conveniently set, and which may also be regulated, cause the piston to be projected, alternatively, outward from an external cylindrical jacket.

As it was previously mentioned, the electromechanical assembly above described is duly controlled by an electronic driving installation, through which the positioning of each of the mobile parts duly bound to the rotating coders and end-of-travel positions is commanded. By way of power control circuits, this installation may also feed the referred electric motors that give place to the movements of the different machine parts.

The electronic installation of the combination of means that the invention machine is comprised of, has been adapted to operate as a remote command which is usually called "remote control".

In this way, a wireless command is created which is embedded into the mentioned electronic installation arranged into the machine, so that the information sent by the user, related both to the positioning of each of the mobile parts and to the speed of the swinging run of the massage piston, is transmitted in a precise, simple, smooth and direct way.

The installation considers the option to save, through memories, the prior adjustment established by the user, so that in next uses, after starting up the machine, the user has the option to order the machine to operate in the pre-established memory point.

In this sense, the invention contemplates that the mentioned electronic installation uses the wireless networks that may be one of the following: Wireless Local Area Network (WLAN), Wireless Wide Area Network (WWAN), Wireless Metropolitan Area Network (WMAN), Wireless Personal Area Network (WPAN) or FR, which in turn will allow the incorporation of study and video equipment that, through theses networks, signals may be received and sent by the users.

Other functions taken into account with the embedded electronic installation consists of controlling and managing the handling of the energy accumulator that feeds all the system. This accumulator, that may be replaced by the user immediately, supplies all the energy required for the compliance with the above mentioned functions, so it is not necessary for the machine to be connected to the mains supply network, thus providing a great peace and extra comfort to the user.

It is also contemplated that the accumulator(s) supplied may be recharged by way of an external charger, or may be provided into the machine.

No any machine for sexual activity presently known proposes, or even suggests, the structural solution that arises from what is mentioned in the preceding paragraphs, that's why it is considered not only a novel proposal but also a clear inventive activity.

BRIEF DESCRIPTION OF THE DRAWINGS

In order to specify the advantages merely mentioned, to which the users and those skilled in the art may add many others more, and to facilitate the understanding of the structural, constitutive and functional characteristics of the electromechanical invention machine, it is below described a preferred example of the embodiment, which is schematically illustrated and without a determined scale, in the attached sheets, with the expressed explanation that just for being an example, no any limited or exclusive character of the protection scope of the present invention may be assigned thereto.

It is clarified that, in all figures, equal reference numbers and letters correspond to the same or equivalent parts or elements that make up the assembly, in accordance with the example chosen for this explanation of the electromechanical machine of the invention.

DETAILED DESCRIPTION OF A PREFERRED EMBODIMENT

As it can be seen in FIGS. 1 to 5, the electromechanical machine with wireless control for sexual activity referred to in the present invention, is comprised of three sections, as follow:

main body identified by the global reference (A),
an intermediate arm identified by the global reference (B),
a head of the massage actuator identified by the global reference (C)

The main body (A) is comprised of a lower flat base (1) that is a support of the whole assembly, being arranged covered by a top lock shell (2).

In order to guarantee stability during use, this lower flat base (1) is coupled to a flat platform (3) of lower support, that, so as to be kept and transported, may be folding from a straight line of central folding (4).

Figure 1:
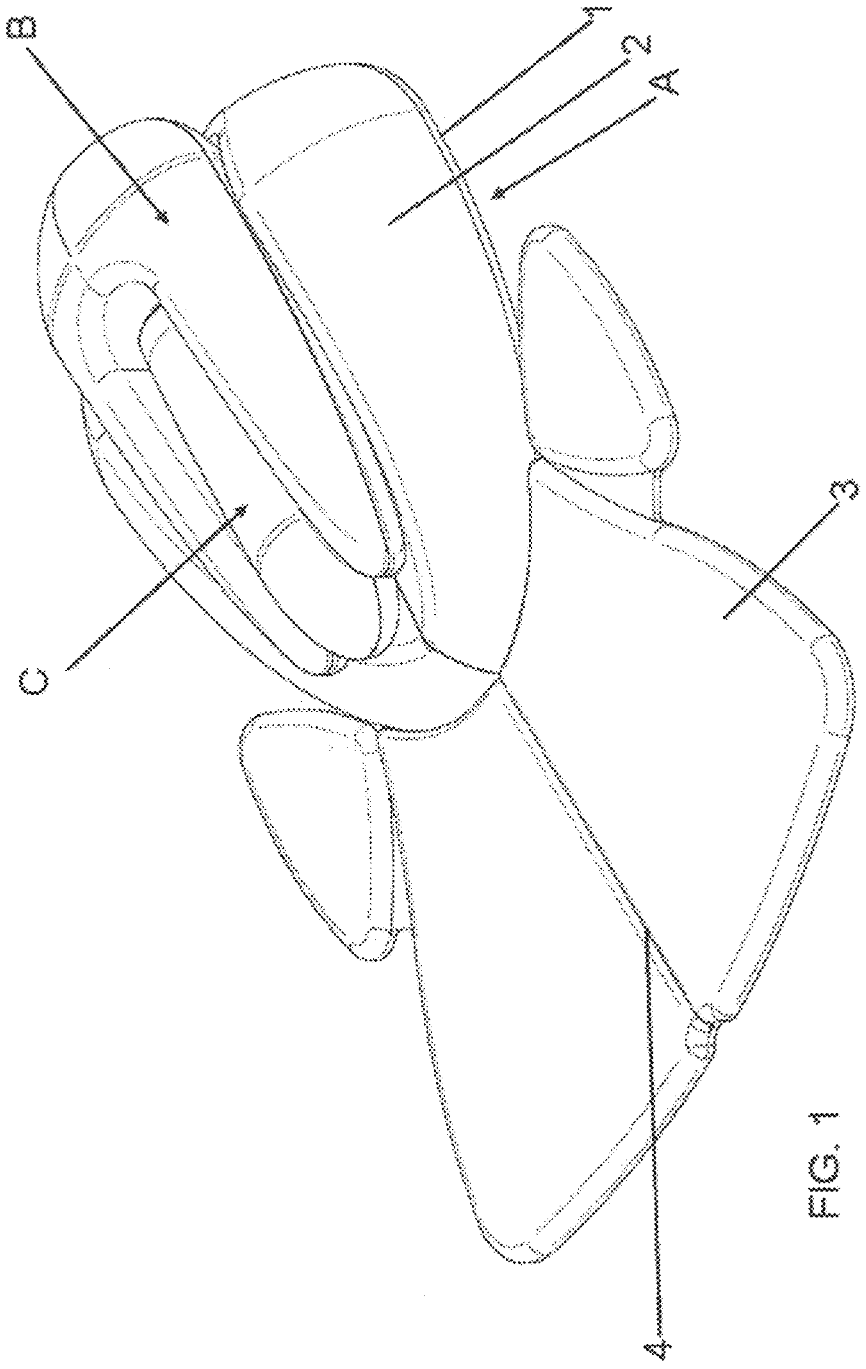
FIG. 1 is a perspective view that shows the machine for sexual activity of the invention with a flat embedded platform.
Figure 2:
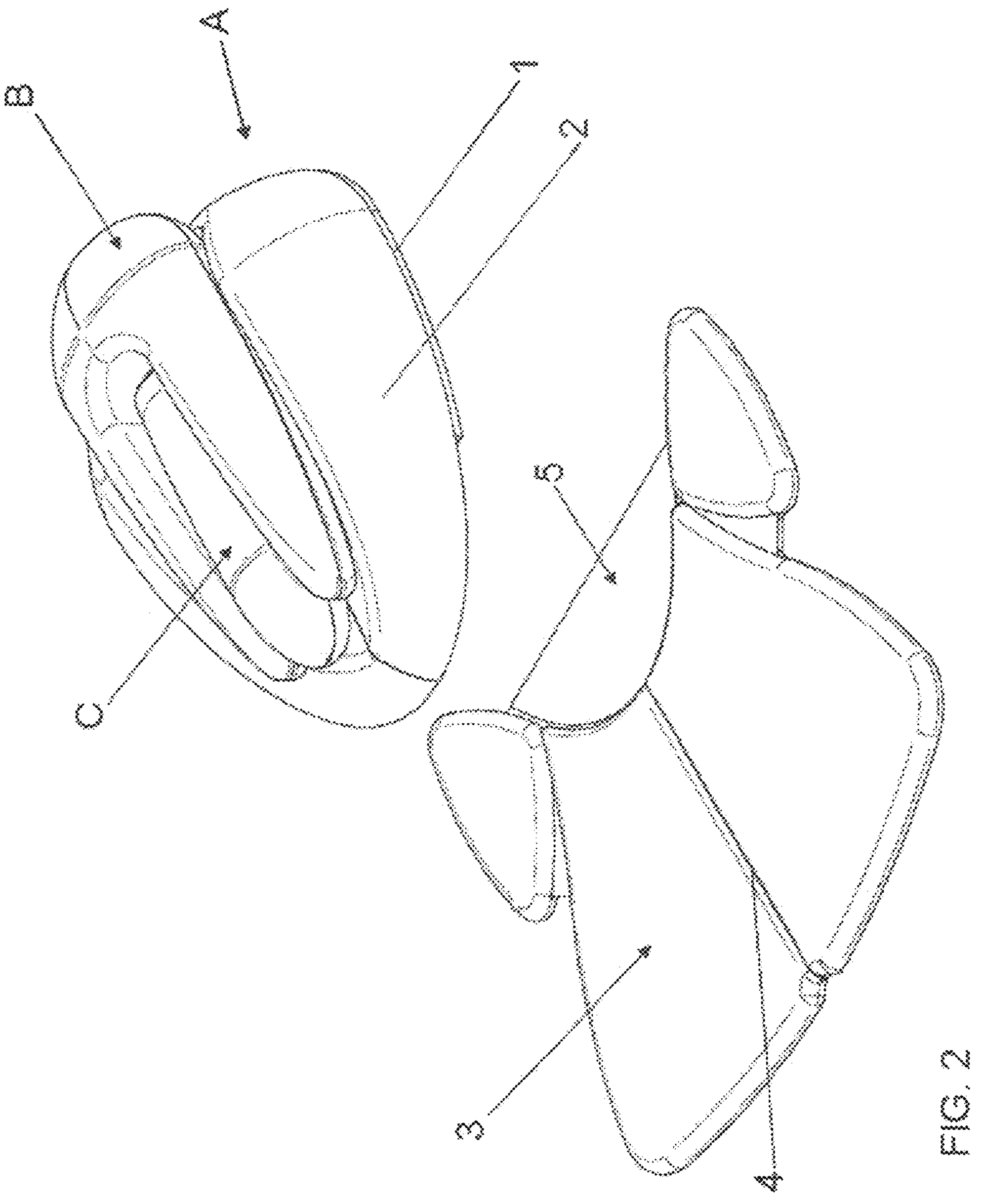
FIG. 2 is also a perspective view that shows the same machine of the prior figure, in this case separated from the support platform thereof.

By specifically looking at FIG. 2, we may appreciate that this platform (3), passing a transverse step, defines a surface (5) specially designed so that the main body (A) may be stood thereon, with the possibility of incorporating fixing means (portions of velcro or magnetic plates) acting as a fast coupling means.

Figure 4:
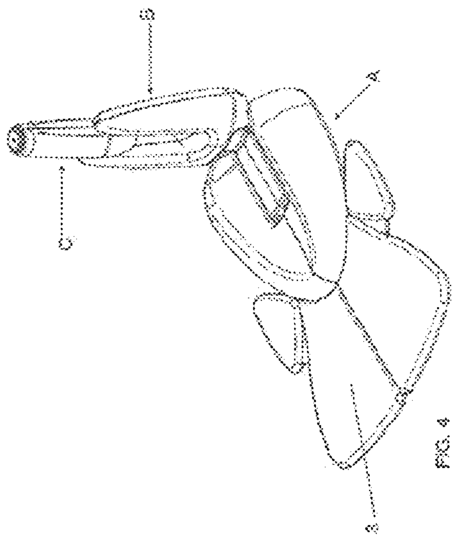
FIG. 4 is also a perspective view that, in this case, represents the same machine of the previous figures in another operative positioning.
Figure 5:
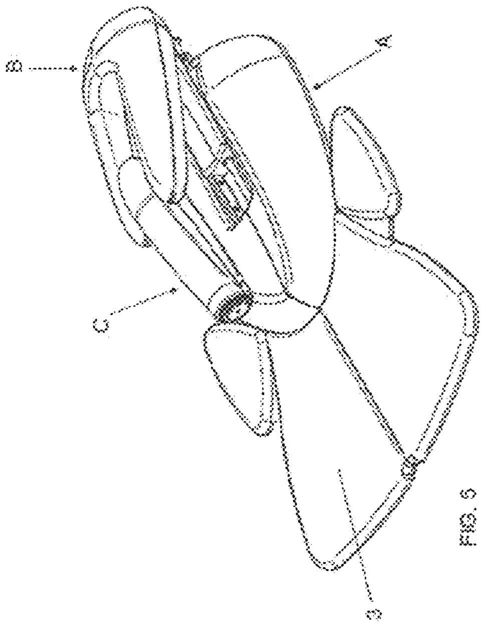
FIG. 5 is also a perspective view that, in this case, represents the same machine of the previous figures in another operative positioning.
Figure 3:
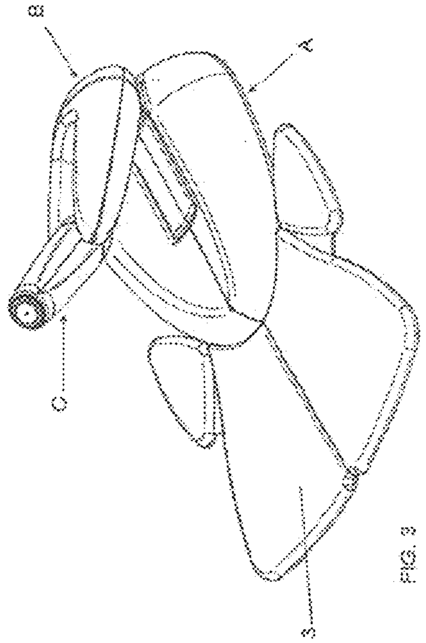
FIG. 3 is also a perspective view that, in this case, represents the same machine of the previous figures in an operative positioning.

Under the conditions exposed and now looking at FIGS. 3, 4 and 5, it is appreciated that the electromechanical machine of the invention, in order to be used for sexual activity, may adopt very variable operative positions, for which various movements of previous positions are combined, as follow:

Movement in the horizontal plane, for which the mentioned main body (A) has a sliding carriage (D) assembled under a sliding condition in straight direction and in both senses.

First angular movement, for which the intermediate arm (B), pivoting in an end of the sliding carriage (D), is assembled into a first dynamic swivel that provides a circular movement, in both senses, in a vertical plane.

Furthermore, the head of the massage actuator (C) makes a second angular movement, by pivoting in the superior end of the intermediate arm (B) and is assembled into a second dynamic swivel that provides a circular movement, in both senses, in the vertical plane.

Figure 6:
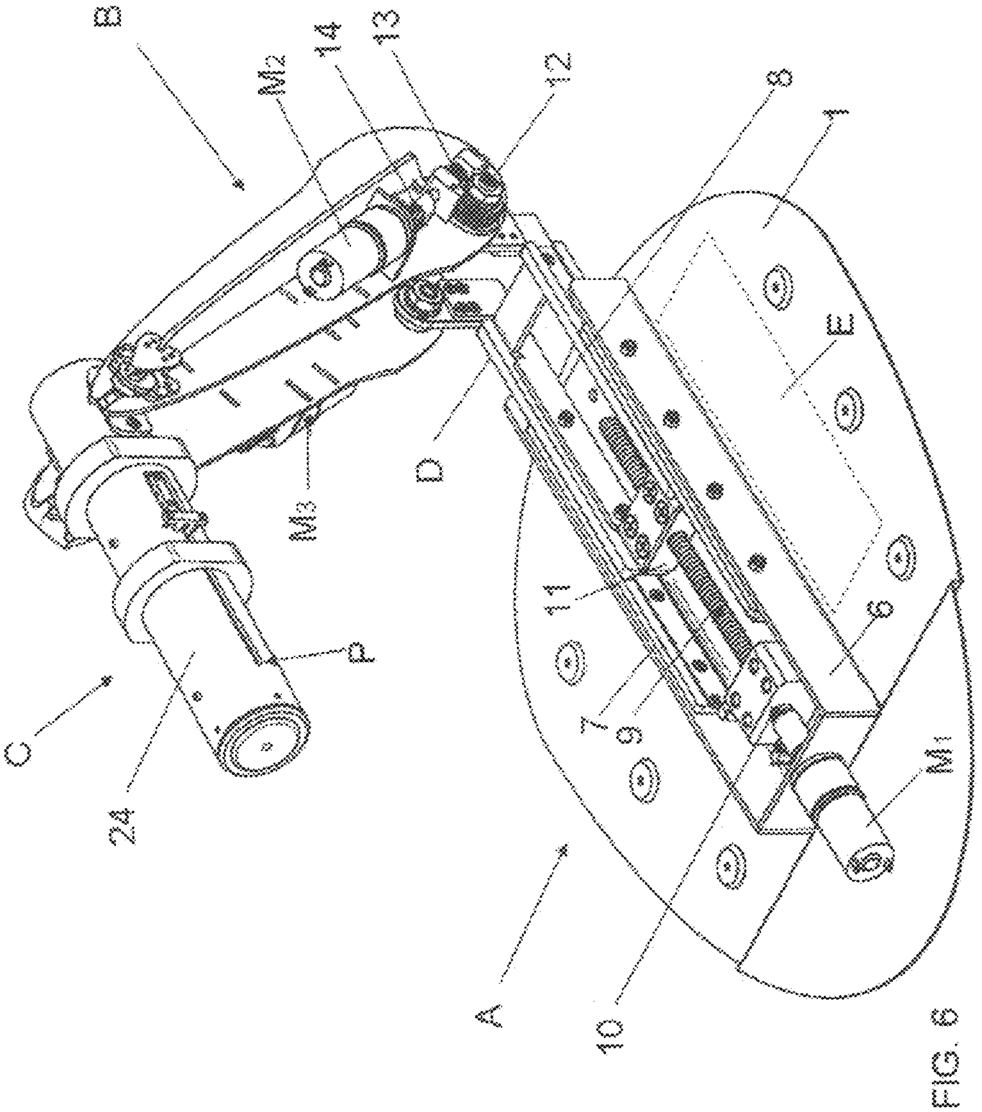
FIG. 6 is also a perspective view of the same machine of the previous figures, without the lock shells, thus being possible to see the combination of basic elements into it.

Now looking at FIG. 6, it is appreciated that the main body (A) presents a fixed frame (6) over which the sliding carriage (D) is assembled running over the side straight guides (7) and (8), that are defined in the internal faces of the longitudinal partitions of the frame.

It is also appreciated that over the same fixed frame (6) the first motor reducer ($M_1$) is assembled, which output axis is extended up to get coupled to the thread worm axis (9), with the corresponding hubs put in between (10).

It can be seen that over said thread worm axis (9) a nut (11) is arranged that makes up the body of said sliding carriage (C) in such a way that with said motor (M1) it is possible to drive the straight movements of the carriage (C) in both senses.

In order to guarantee that these movements do not cause undesirable related movements, in preferred embodiments, the carriage support over the long guides (7) and (8) of the frame (6) will be made by using the superior and lower edges of each guide, and using a dovetail type assembly as in this way all the side movements such as the headbanging are counteracted.

In this FIG. 6 it is appreciated that the main body (A) also houses the electronic elements (E) that command all the motors and sensors and from where the communication is generated to the external devices, such as the remote wireless command (R) (visible in FIGS. 14 to 17).

Figure 8:
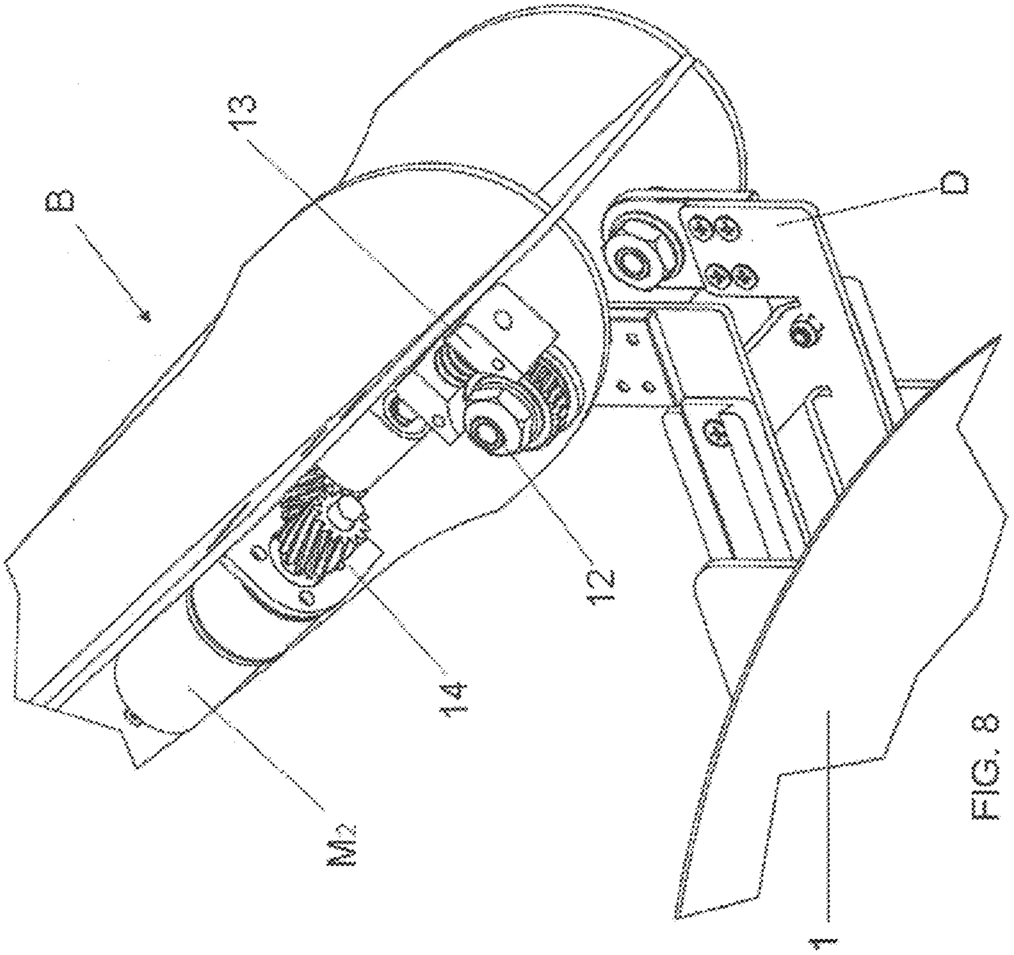
FIG. 8 is an enlarged detail of a portion of the invention machine, under reference (VIII) in FIG. 7.
Figure 7:
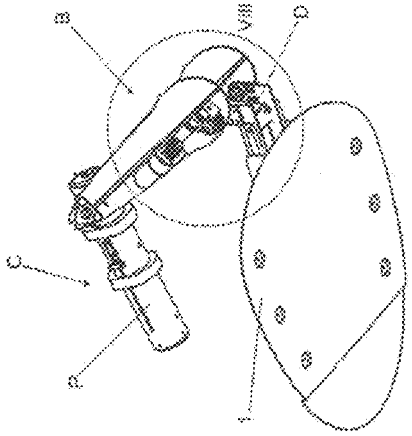
FIG. 7 is a perspective view that globally represents and without an end shell two of the sections comprising thereof.

Now looking at FIGS. 6, 7 and 8 it is possible to appreciate how the assembly and the operation of the mentioned intermediate arm (B) is made, that sets the second section of the machine for sexual activity of the invention.

It is appreciated that the lower end of the mentioned intermediate arm (B) is assembled into an and of the sliding carriage (D) by way of a pair of transverse pivoting axis, of which, that represented by reference (12) is associated with a mechanism of crown and worm (13) where the worm is extended to be coupled to the gears (14) bound to the output axis of the second motor reducer ($M_2$).

It is clear that, through this motor reducer ($M_2$) it is possible to drive the angular movements, in the vertical plane with circular direction and also in both senses, of the referred intermediate arm (B) and therefore to establish the second adjustment of the previous positioning.

Figure 10:
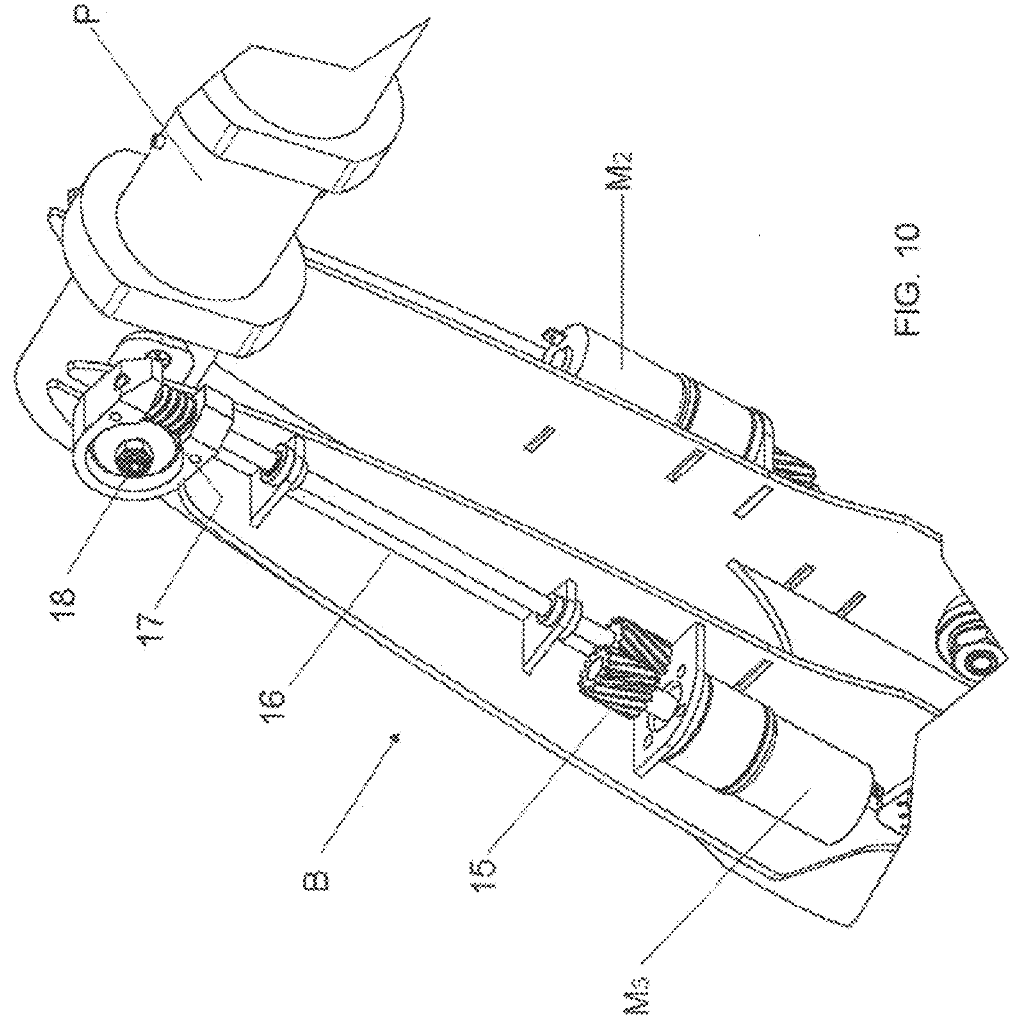
FIG. 10 is an enlarged detail of a portion of the invention machine, under reference (X) in FIG. 9.
Figure 9:
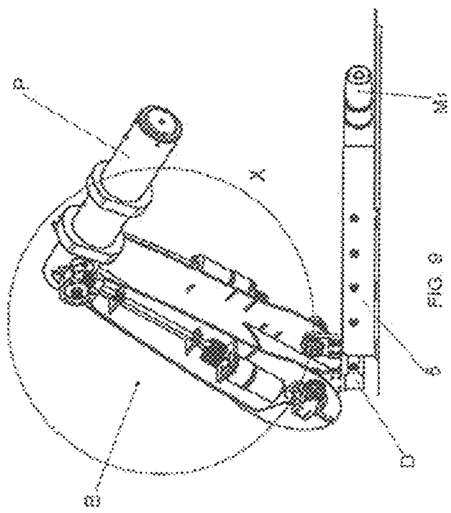
FIG. 9 is a perspective view that globally represents and without a shell of termination, the three sections comprising thereof.
Figure 11:
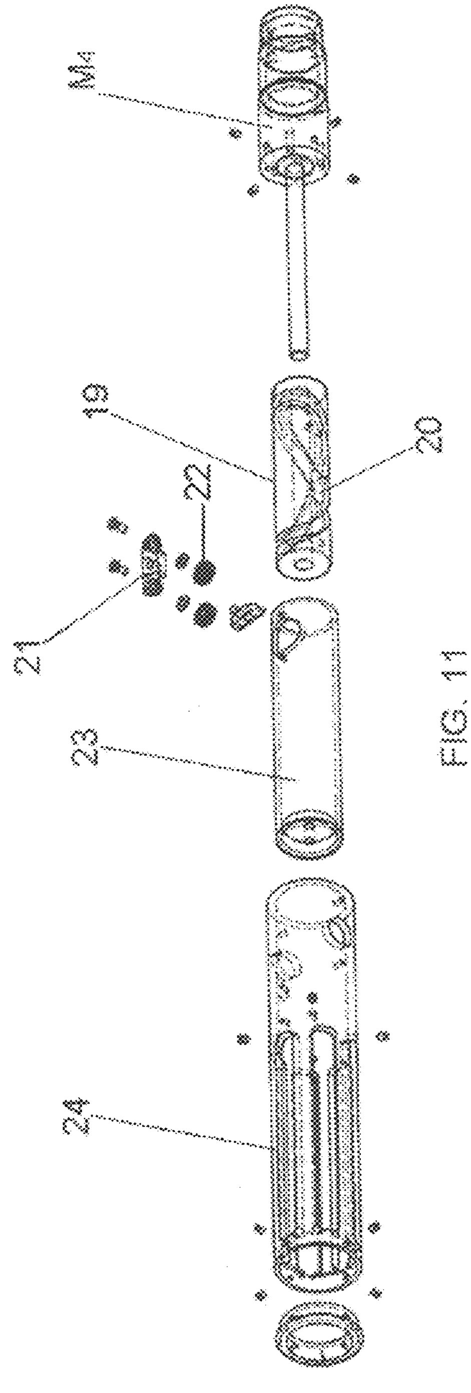
FIG. 11 is an exploded perspective view where it can be seen those basic elements that take part to form the head of the massage actuator that is included in the electromechanical machine of this invention.
Figure 12:
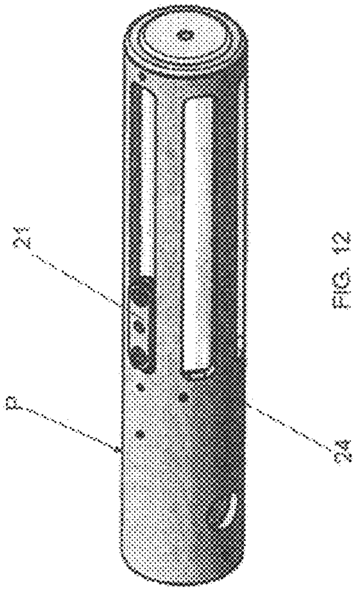
FIG. 12 is a perspective view that shows the piston incorporated into the head of the massage actuator of the invention machine.
Figure 13:
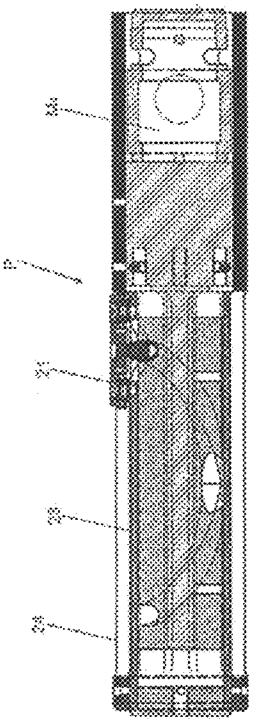
FIG. 13 is a cross-sectional schematic view that shows the same head of the massage actuator of the previous figures.
Figure 14:
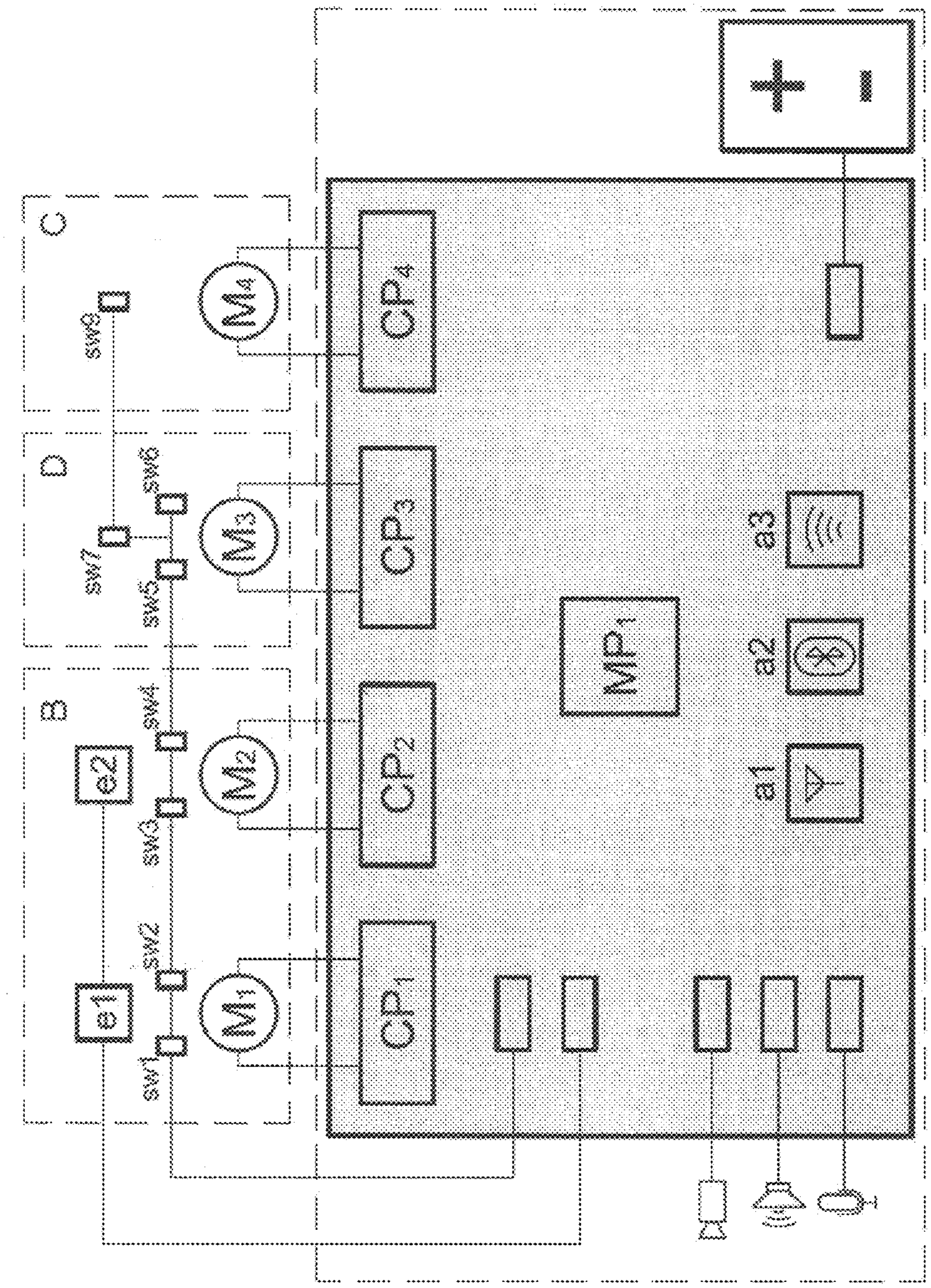
FIG. 14 is a chart that shows how the controlling plate that makes up the electronic driving installation of the invention machine is comprised of FIG. 15 is a chart that represents the anterior face of the electronic device that forms the remote control that uses the electronic driving installation of the invention machine.
Figure 17:
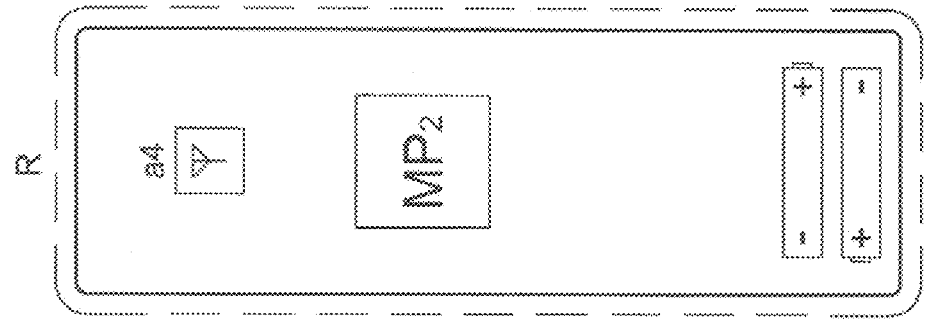
FIG. 17 is a chart that represents the back face of the electronic device that forms the remote control that uses the electronic driving installation of the invention machine.

Now by looking at FIGS. 6, 9 and 10 it may be understood that the same intermediate arm (B), at its superior end, is bound to the third section (C) of the electromechanical machine of the invention, through a second dynamic swivel.

It can be seen that said arm (B) includes a third motor reducer ($M_3$) which output axis is coupled to the gears (15) that transmit the movement of the axis (16) extending up to the crown/worm system (17) associated to the pivoting axis (18) where the head of the massage actuator (C) is assembled.

It is appreciated that, through this motor reducer (M3) it is possible to drive the angular movements, in the vertical plane with circular direction and also in both senses, of the referred head of the massage actuator (C) and therefore to establish the second adjustment of the previous positioning.

It is specially emphasized the great advantage that the invention machine presents due to the fact that by driving the referred motors reducers ($M_1$), ($M_2$) and ($M_3$), it is possible to establish different operative positions that are individually chosen by each user in a precise, simple and direct way.

Now looking at FIGS. 6, 11, 12 and 13, it is appreciated how the third section that makes up the invention machine is formed and it is called the head of the massage actuator (C).

The mechanical assembly named piston (P) is located into the head, its function is to transform the rotating movement of the output axis of the motor reducer ($M_4$), into a linear alternative movement.

So, the output axis of said motor reducer $M_4$) is associated with a hollow axis (19) which cylindrical surface is affected by a longitudinal groove (20) that follows a curved line such as a continuous sinusoidal propeller (worm).

Above said helical groove (20), a sliding skid (21) runs, conveniently assembled over bearings (22), which is associated with the cylindrical and enlarged body of the massage piston (23), and provides the traditional swinging linear movement.

Under the conditions mentioned, said piston for massage (23) held by the cylindrical jacket (24), will have a linear movement through which the piston body is projected outward, forward and backward.

Now looking at the charts represented by FIGS. 14 to 17, it is possible to appreciate how the electronic installation of command and drive, being used by the invention machine, is made up, as a part of the combination of means that are a part thereof.

It may be seen that the electronic controlling plate (E) installed in the main body (A) is holding a remote control processor ($MP_2$) that receives the order, processes the information and sends it through the FR antenna (a4) of the remote control (R), to the FR antenna (a1) of the electronic system (E) installed into the machine, that communicates the information to the processor ($MP_1$).

Said processor ($MP_1$) checks the status of the sensors (e1), (e2) y (sw1), (sw2, (sw3), (sw4), (sw5), (sw6), (sw7) and (sw9). If said processor detects that the position of all the mobile parts are in their place, it deploys the machine, by way of the power controls command (CP1), (CP2), (CP3 and (CP4) and activates the operation of the motor reducers ($M_1$), ($M_2$) and ($M_3$) by arranging all its mobiles parts to the "on" position to be commanded from the same remote control (R) (visible in FIG. 15).

Once the "on" position is determined, each time the key in the remote control (R) in the sections: carriage (D), intermediate arm (B) and head of massage actuator (C) is pressed the procedure that modifies the position of the mobile parts is repeated and the position of each part at each time is registered again.

The motor reducer ($M_4$) will not be activated until the keys located in the section piston (P) are pressed. When these keys are pressed, the previously described mechanism of the piston (P) will start moving, thus activating the swinging rectilinear movement of the massage piston (23) that is activated therewith.

While the referred motor reducer ($M_4$) is active, any pressure over the keys of the sections (D) carriage, (B) arm and (C) head, will be null as it may cause damage to the user. Only after pressing the key represented by reference (X) in the section piston (P) and once said piston working is stopped, the machine will be able to freely move the carriage (D), the arm (B) and the head of the massage actuator (C) in order to command new positionings.

Figure 16:
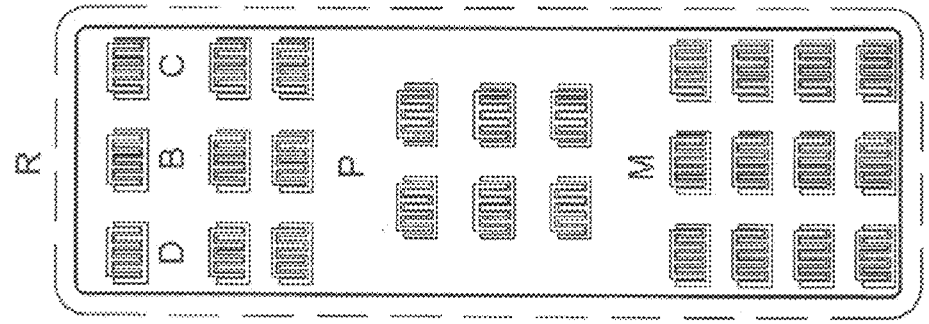
FIG. 16 is a chart that represents the electronic controlling plate of the same remote control that uses the electronic driving installation of the invention machine.
Figure 15:
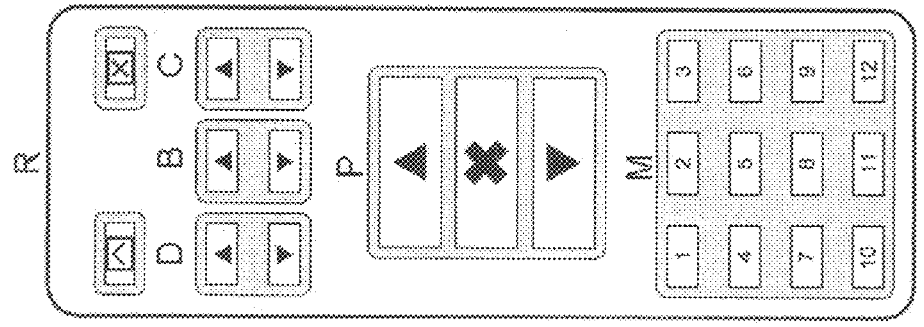

By looking at FIGS. 15 and 16, it is possible to understand that buttons (1) to (12) of the section memories (M) of the remote control are only used when the machine is "on" and the piston (P) is stopped.

These keys have a double functioning:

a) when pressure is applied during a time less than five seconds, and b) when the same pressure is applied during more than five seconds.

Pressure of any key of the section memories (M) during less than five seconds will cause the mobile parts respectively bound to each other to move to the position saved for this key.

Pressure applied for more than five seconds will save the position of each of the mobile parts respectively bound to each other at that time to be called afterwards.

Once the electronic installation of command and drive is so formed, when the machine is on by pressing the key (TE) of the remote control (R), then the installation is ready for the user to position the parts carriage (D), arm (B) and actuator head (C) by using the respective keys (visible in FIG. 15).

In this way, the user calibrates the position of the referred sections thereof to be arranged in the desired position (as it is shown in FIGS. 3, 4 and 5).

Immediately after the user shall press, during more than five seconds, the key of the section memories (M) with the number (1), in which case the established order is saved. Let's call this moment "instant 1".

Subsequently, it will be possible to move each one of the mobile parts to the other positions by using the keys of the sections carriage (D), arm (B) and actuator head (C), also to deactivate the machine, to withdraw the energy accumulator and keep it in its box.

If at any time when the machine is used again, decision is made to position the machine as it was positioned in the "instant 1", by pressing the key (1) during less than five seconds the machine will automatically modify the position of all its parts to accommodate to the position in which it was at the time the memory (1) was saved.

The other keys of the section memories (M) work in the same way.

In this preferred example of embodiment, it is presented the case wherein the machine is set with twelve previously saved positions that may be modified by the user with the prior procedure. Only the combination of the keys (1) and (12) during more than ten seconds will delete the memories programmed by the user and will return to the default values.

Having described and exemplified the nature and main object of the present invention, as well as the way in which it may be put into practice, exclusive rights and ownership are hereby claimed:

1. An ELECTROMECHANICAL MACHINE WITH WIRELESS CONTROL FOR SEXUAL ACTIVITY, that combines three sections bound to each other by the corresponding dynamic swivels that are driven from a remote control of adjustment and command, characterized in that the first section constitutes the main body wherein a fixed frame whereby a sliding carriage is defined, which is arranged associated with a first motor reducer which drives its rectilinear movement, in the horizontal plane and in both senses; said sliding carriage, by one end, is bound to an intermediate arm, which makes up the second section of the machine, being arranged over a pivoting transverse axis that is into a first dynamic swivel, which is arranged associated to a second driving motor reducer so that said intermediate arm may make a pivoting movement in the vertical plane, with circular direction in both senses; said intermediate arm, by its other end, is bound to a head of the massage actuator, that makes up the third section of the machine, being arranged over a transverse axis that forms a second dynamic swivel, which is arranged associated to a third driving motor reducer so that said head of massage actuator may make a pivoting movement in the vertical plane, with circular direction in both senses; an actuator piston is arranged into the head of the massage actuator which transforms the rotating movement that transmits the output axis of a fourth motor reducer into an alternative linear movement that is transmitted to the piston for massage; constituting the four motor reducers an electronic driving installation by remote control, through which the positioning of each of the mobile parts duly bound to the rotating coders and end-of-travel positions is commanded.

2. The ELECTROMECHANICAL MACHINE WITH WIRELESS CONTROL FOR SEXUAL ACTIVITY, in accordance with what is claimed in claim 1, characterized in that the first motor reducer has its output axis coupled to a worm over which a nut associated with the sliding carriage is run, which is arranged supported by longitudinal movement guides defined in the fixed frame that is defined in the main body.

3. The ELECTROMECHANICAL MACHINE WITH WIRELESS CONTROL FOR SEXUAL ACTIVITY, in accordance with what is claimed in claim 1, characterized in that the second motor reducer, has an output axis with a gears train and a corresponding assembly of crown and worm, through which the rotating movement is transmitted to the pivoting axis of the intermediate arm.

4. The ELECTROMECHANICAL MACHINE WITH WIRELESS CONTROL FOR SEXUAL ACTIVITY, in accordance with what is claimed in claim 1, characterized in that the third motor reducer, has an output axis with a gears train that transmits the movement to a corresponding assembly of crown and worm that transfers the rotating movement to the pivoting axis of the head of massage actuator.

5. The ELECTROMECHANICAL MACHINE WITH WIRELESS CONTROL FOR SEXUAL ACTIVITY, in accordance with what is claimed in claim 1, characterized in that the output axis of a fourth motor reducer is associated to a hollow axis which cylindrical surface is affected by a longitudinal groove that follows a curved line such as a continuous sinusoidal propeller over which a sliding skid is associated with the cylindrical and enlarged body of the piston for massage, and provides the swinging linear movement.

6. The ELECTROMECHANICAL MACHINE WITH WIRELESS CONTROL FOR SEXUAL ACTIVITY, in accordance with what is claimed in claim 1, characterized in that the run of the massage piston, in its swinging movement, is made from a cylindrical jacket that sets the external face of the piston for massage.

7. The ELECTROMECHANICAL MACHINE WITH WIRELESS CONTROL FOR SEXUAL ACTIVITY, in accordance with what is claimed in claim 1, characterized in that the electronic driving installation is comprised of an electronic controlling plate (E) installed in the main body (A) and includes a remote control processor ($MP_2$) that receives the order, processes the information and sends it through the FR antenna (a4) of the remote control (R), to the FR antenna (a1) of the electronic system (E) installed into the machine, that communicates the information to its processor ($MP_1$).

8. The ELECTROMECHANICAL MACHINE WITH WIRELESS CONTROL FOR SEXUAL ACTIVITY, in accordance with what is claimed in claim 1, characterized in that the electronic installation of remote control includes the option of saving, through memories, the previous adjustment that the user establishes in each case.

* * * * *